United States Patent
Fujisawa

(10) Patent No.: US 9,710,904 B2
(45) Date of Patent: Jul. 18, 2017

(54) TIRE APPEARANCE INSPECTION APPARATUS

(71) Applicant: BRIDGESTONE CORPORATION, Tokyo (JP)

(72) Inventor: Yoshitaka Fujisawa, Kodaira (JP)

(73) Assignee: BRIDGESTONE CORPORATION, Tokyo (JP)

(*) Notice: Subject to any disclaimer, the term of this patent is extended or adjusted under 35 U.S.C. 154(b) by 0 days.

(21) Appl. No.: 14/783,291

(22) PCT Filed: Apr. 25, 2014

(86) PCT No.: PCT/JP2014/061664
§ 371 (c)(1),
(2) Date: Nov. 20, 2015

(87) PCT Pub. No.: WO2014/175413
PCT Pub. Date: Oct. 30, 2014

(65) Prior Publication Data
US 2016/0086320 A1 Mar. 24, 2016

(30) Foreign Application Priority Data
Apr. 25, 2013 (JP) ................. 2013-092438

(51) Int. Cl.
| | | |
|---|---|---|
| G06K 9/00 | (2006.01) |
| G06T 7/00 | (2017.01) |
| G01N 21/956 | (2006.01) |
| G06K 9/62 | (2006.01) |
| G01B 11/24 | (2006.01) |

(Continued)

(52) U.S. Cl.
CPC ............. G06T 7/001 (2013.01); G01B 11/24 (2013.01); G01N 21/8851 (2013.01);
(Continued)

(58) Field of Classification Search
None
See application file for complete search history.

(56) References Cited

U.S. PATENT DOCUMENTS 5,073,952 A * 12/1991 Watanabe ............... G06T 7/001
348/129
2006/0050267 A1* 3/2006 Murakami ............ G06T 7/0008
356/237.2

(Continued)

FOREIGN PATENT DOCUMENTS

EP 1 750 089 A1 2/2007
JP H09-318555 A 12/1997
(Continued)

OTHER PUBLICATIONS

Jun. 1, 2016 extended Search Report issued in European Patent Application No. 14787947.2.
(Continued)

Primary Examiner — Hadi Akhavannik
(74) Attorney, Agent, or Firm — Oliff PLC

(57) ABSTRACT

An inspection apparatus capable of preventing a conforming article from being judged as nonconforming when inspecting a molded object for acceptability by performing image processing on an image captured of the inspection object. The apparatus includes a means for positioning a model pattern in a position with a highest degree of agreement by matching the model pattern against the image captured of the inspection object, a model pattern dividing means for dividing the model pattern into a plurality of elements in such a manner as to have mutually overlapping regions, and a shape recognition means for recognizing a shape corresponding to the model pattern by positioning each of the elements divided by the model pattern dividing means in a position with a highest degree of agreement by performing pattern matching within a predetermined range with reference to the position where the model pattern has been positioned on the image.

3 Claims, 2 Drawing Sheets

(51) Int. Cl.
- *G01N 21/88* (2006.01)
- *G06K 9/46* (2006.01)
- *G06T 7/73* (2017.01)
- *G06T 7/11* (2017.01)
- *G06T 7/13* (2017.01)

(52) U.S. Cl.
CPC ..... *G01N 21/95607* (2013.01); *G06K 9/4604* (2013.01); *G06K 9/6201* (2013.01); *G06K 9/6211* (2013.01); *G06T 7/11* (2017.01); *G06T 7/13* (2017.01); *G06T 7/74* (2017.01); *G01N 2201/12* (2013.01); *G06K 2009/4666* (2013.01); *G06T 2207/20112* (2013.01); *G06T 2207/30108* (2013.01)

(56) References Cited

U.S. PATENT DOCUMENTS

| | | | |
|---|---|---|---|
| 2007/0209431 A1 | 9/2007 | Fujisawa et al. | |
| 2009/0279772 A1* | 11/2009 | Sun | G06K 9/6298 382/141 |
| 2011/0019903 A1 | 1/2011 | Joly et al. | |
| 2011/0142326 A1* | 6/2011 | Shinoda | G06T 7/001 382/149 |
| 2013/0336575 A1* | 12/2013 | Dalla-Torre | G06T 7/001 382/149 |

FOREIGN PATENT DOCUMENTS

| | | |
|---|---|---|
| JP | 2005-331274 A | 12/2005 |
| JP | 2006-275952 A | 10/2006 |
| JP | 2011-509398 A | 3/2011 |
| JP | 2011-112398 A | 6/2011 |

OTHER PUBLICATIONS

Translation of Oct. 27, 2015 International Preliminary Report on Patentability issued in International Patent Application No. PCT/JP2014/061664.

Jul. 1, 2014 Search Report issued in International Patent Application No. PCT/JP2014/061664.

* cited by examiner

TIRE APPEARANCE INSPECTION APPARATUS

TECHNICAL FIELD

The present invention relates to an inspection apparatus capable of preventing a conforming article from being judged nonconforming when inspecting a molded product for acceptability by performing image processing on an image captured of the appearance of the inspection object.

BACKGROUND ART

An inspection apparatus known in the art determines the acceptability of an inspection object by storing conforming article data, as a model pattern, of the inspection object, such as molded characters on a product, and calculating the degree of agreement between the image pattern obtained of the inspection object and the model pattern (see Patent Document 1).

However, in such an inspection, some products, which are in fact conforming units, may show low degrees of agreement between the image pattern of the inspection object and the model pattern. Such situations may sometimes lead to judgment of conforming articles as nonconforming. For example, let us assume an inspection for acceptability of the molded state of a character an inspection for acceptability of the molded state of a character string, which is an inspection object with protrusions and recesses molded on the side of the tire. Tires before such inspection are placed in a certain location temporarily, and, as a result, the sides of tires can get deformed by the sagging of the rubber or the overlap of belts. ?? With a character string molded on the side of a tire deformed as described above, there will be drops in the degree of agreement of the model pattern with the image pattern of the character string. Consequently, it may be possible that the character string molded correctly on the side of a tire is judged as nonconforming.

PRIOR ART DOCUMENT

Patent Document

Patent Document 1: Japanese Unexamined Patent Application Publication No. 2006-275952

SUMMARY OF THE INVENTION

Problems to Be Solved By the Invention

The purpose of this invention is therefore to provide an inspection apparatus capable of preventing a conforming article from being judged nonconforming when inspecting a molded object for acceptability by performing image processing on an image captured of the inspection object.

Means for Solving the Problem

Thus, an inspection apparatus to solve the above-described problem includes a model pattern positioning means for positioning a model pattern in a position with a highest degree of agreement by matching the model pattern against the image captured of the appearance of an inspection object, a model pattern dividing means for dividing the model pattern into a plurality of elements in such a manner as to have mutually overlapping regions, and a shape recognition means for recognizing a shape corresponding to the model pattern by positioning each of the elements divided by the model pattern dividing means in a position with a highest degree of agreement by performing pattern matching within a predetermined range with reference to the position where the model pattern has been positioned on the image. As a result, it is possible to perform pattern matching of elements, which are the divisions of the model pattern, accurately with the image captured even when the image of the inspection object, which is in fact a conforming article, has been captured with deformity. Accordingly, it is possible to prevent a conforming inspection object from being judged as nonconforming because the model pattern is not well matched to the image.

BEST MODE FOR CARRYING OUT THE INVENTION

First Embodiment

Figure 1:
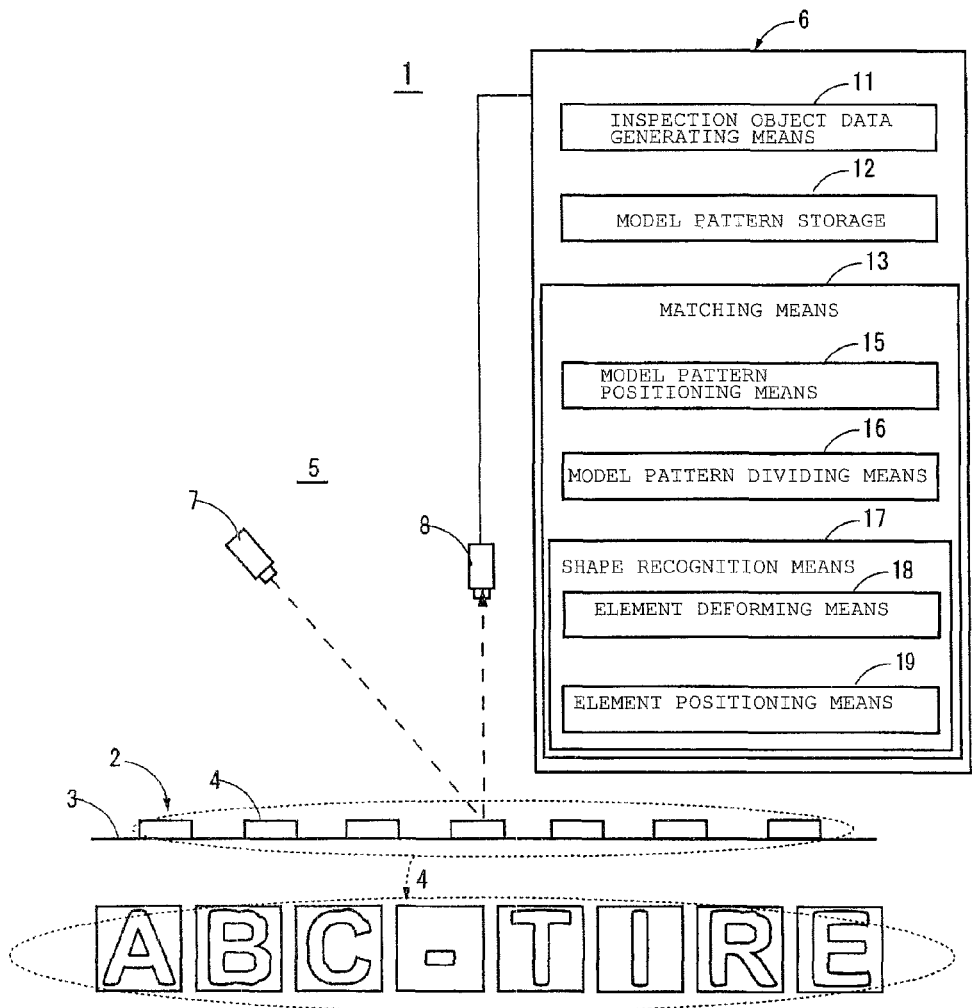
FIG. 1 is a schematic configuration diagram showing a block constitution of an inspection apparatus.

FIG. 1 is a schematic configuration diagram of an inspection apparatus 1 for a tire 2 implementing an embodiment of the present invention. As shown in FIG. 1, the inspection apparatus 1 according to the first embodiment is an apparatus for inspecting for acceptability each of molded characters, which constitute a character string 4 with protrusions and recesses molded on the side 3 of the tire 2. The tire 2 in this case is supposed to be one having a deformed side 3 because it has been placed after manufacture temporarily in a certain location before the inspection. The inspection apparatus 1 has an inspection object imaging unit 5 for capturing an image of the character string 4 on the side 3 of a "not inflated" tire 2 and a pattern matching unit 6.

The inspection object imaging unit 5 comprises a unit for capturing the whole image of the character string 4 by optical cutting method (light-section method), for instance. The unit consists of a laser unit 7 for emitting a laser beam at the character string 4 and a camera 8 for imaging the character string 4 irradiated with the laser beam. Thus an image of the side 3 of the tire 2 including the character string 4 molded thereon is captured.

The pattern matching unit 6 includes an image pattern generating means 11, a model pattern storage 12 for storing a model pattern M of the character string 4, and a matching means 13.

The image pattern generating means 11 derives the shape data of the character string 4 from the image captured by the inspection object imaging unit 5 and at the same time generates an image pattern R from the feature points of the shape data necessary for recognizing the shape of each character in the character string 4.

Figure 2A:
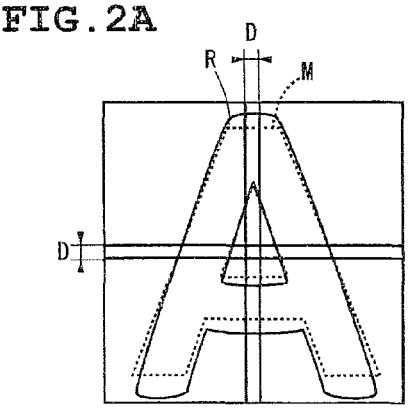
FIG. 2 is diagrams showing relationship of an image pattern and a model pattern and the division of a model pattern.
Figure 2B:
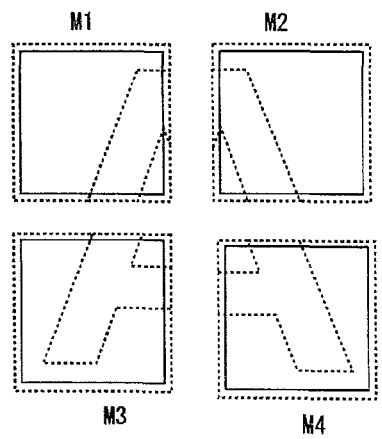

The matching means 13 includes a model pattern positioning means 15 for positioning the model pattern M in a position with a highest degree of agreement by matching the model pattern M indicated by a dotted line against an image pattern R indicated by a solid line on an image as shown in FIG. 2A, a model pattern dividing means 16 for dividing the model pattern M into a plurality of elements M1 to M1 in such a manner as to have mutually overlapping regions D as shown in FIG. 2B, and a shape recognition means 17 for recognizing a shape corresponding to the model pattern M from the image by positioning each of the elements M1 to M4 divided by the model pattern dividing means 16 in a position with a highest degree of agreement by performing pattern matching within a predetermined range with reference to the position where the model pattern has been positioned on the image.

The above-described means 11, 13, and 15 through 17 are realized by a computer and programs to have the computer execute processing procedures by the means 11, 13, and 15 through 17 to be discussed later.

The model pattern positioning means 15 performs pattern matching by moving in pixels the model pattern M of an entire character string 4 on the image captured by the inspection object imaging unit 5. In doing so, the model pattern positioning means 15 calculates the degrees of agreement of the model pattern M with the image pattern R on the image on which the model pattern M is placed and positions the model pattern M in a position with the highest degree of agreement with the image pattern R.

This model pattern M is positioned on the image with the median point of the model pattern M as a reference position, for instance. That is, the model pattern M is set on the image by searching for the image pattern R with the highest degree of agreement with the model pattern M from the image.

The model pattern dividing means 16 divides the model pattern M into a plurality of elements M1 to M4 in equal size in such a manner as to have mutually overlapping regions D as shown in FIGS. 2A and 2B. The overlapping regions D are so set as to create an overlap of a predetermined number of pixels for the neighboring elements M1 to M4. The overlapping regions D provided for the divided elements M1 to M4 in this way can prevent gaps from occurring between the neighboring elements M1 to M4 when the elements M1 to M4 are matched against the image pattern R. That is, the setting of overlapping regions D can prevent a mistaken judgment of nonconformity, which can occur when there are gaps between the neighboring elements M1 to M4.

The shape recognition means 17 includes an element deforming means 18 and an element positioning means 19.

Figure 3A:
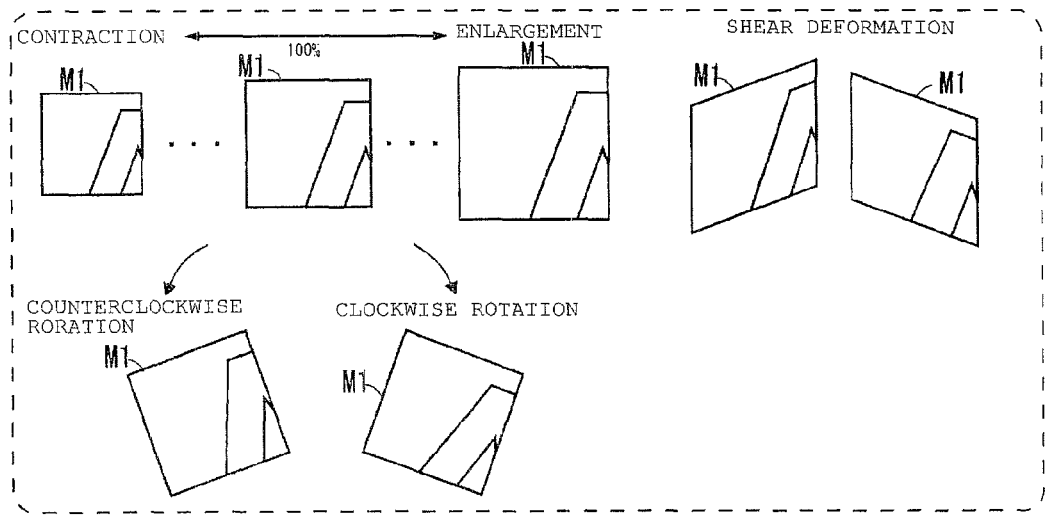
FIG. 3 is diagrams showing a matching of elements to an image pattern.
Figure 3B:
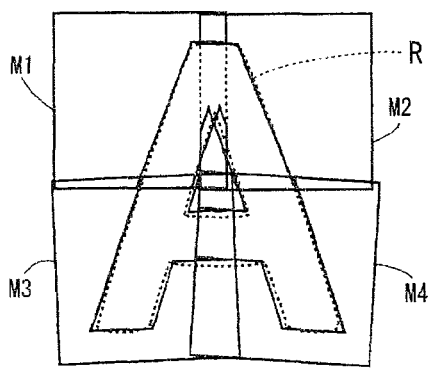

The element deforming means 18 performs predetermined deformations on the elements M1 to M4. More specifically, as shown in FIG. 3A, the element deforming means 18 performs scaling deformation, rotational deformation, shear deformation, or deformation combining them in predetermined proportions on the elements M1 to M4.

The element positioning means 19 performs pattern matching against the image pattern R by deforming the elements M1 to M4 by the element deforming means 18. In this pattern matching, all the above-mentioned deformations on the elements M1 to M4 may be repeated by the element deforming means 18 until a shape showing a highest degree of agreement is obtained. The degree of agreement is calculated as the position of each of the elements M1 to M4 is changed in pixels within a predetermined range with reference to the positions of the elements M1 to M4 when the model pattern M has been positioned against the image pattern R. Following this, the shape recognition means 17 performs positioning of each of the elements M1 to M4 against the image pattern R through further pattern matching of each of the elements M1 to M4 against the image pattern R. Thus, the shape recognition means 17 determines whether the image pattern R has a shape corresponding to the model pattern M. In this manner, pattern matching against the image pattern R is performed by deforming the elements M1 to M4 such that the elements M1 to M4 can be matched to the image pattern R with improved accuracy. In other words, the elements can be matched to the inspection object with better accuracy.

A description is given of the operation of the matching means 13.

The model pattern positioning means 15 positions the model pattern M on the image in a position of the image pattern R where the degree of agreement with the model pattern M is the highest. ?

Next, the elements M1 to M4 of the model pattern M divided by the model pattern dividing means 16 are individually subjected to shape deformation such as scaling deformation, shear deformation, rotational deformation, or a combination of them by the element deforming means 18. Through this, a pattern matching is performed within a predetermined search range with reference to the position where the model pattern M has been positioned. And the elements M1 to M4 are arranged on the image pattern R in the shape of the elements M1 to M4 showing the highest degree of agreement with the image pattern R and are recognized as the respective parts of a character corresponding to the model pattern M.

For example, let us assume that the character "A", indicated by a dotted line, of the character string 4 of the model pattern M positioned on the image by the model pattern positioning means 15 is positioned on the "A", indicated by a solid line, of the image pattern R.

In this case, the element positioning means 19 calculates the degree of agreement of the element M1 constituting a part of the character "A" whenever the "A" of the character string 4 of the model pattern M is moved in pixels from the median point within the search range. Further, as the element deforming means 18 continues to deform the element M1, calculations are performed of the degree of agreement of the element M1 of the "A" of the model pattern M with the image pattern R in the image position where the element M1 is overlapped with the image pattern R. And the image pattern R in the image position and shape showing the highest degree of agreement with the element M1 of the model pattern M is recognized as the character element corresponding to the element M1 of the model pattern M. This process is repeated in the same way for the elements M2 to M4 to recognize the image pattern R (character) corresponding to the model pattern M.

As described above, the degree of agreement can be enhanced by improving the accuracy of positioning the elements M1 to M4 divided by the model pattern dividing means 16 on the image pattern R even when the side 3 of the tire 2 is deformed. It is now possible to match the model pattern M against the image pattern R with accuracy. Thus a mistaken judgment of the character string 4 on the side 3 as nonconforming due to a failure to match the model pattern M with the image pattern R can be prevented even though the character string 4 is, in fact, correctly molded on the side 3 and is therefore conforming for actual use.

Second Embodiment

Figure 4:
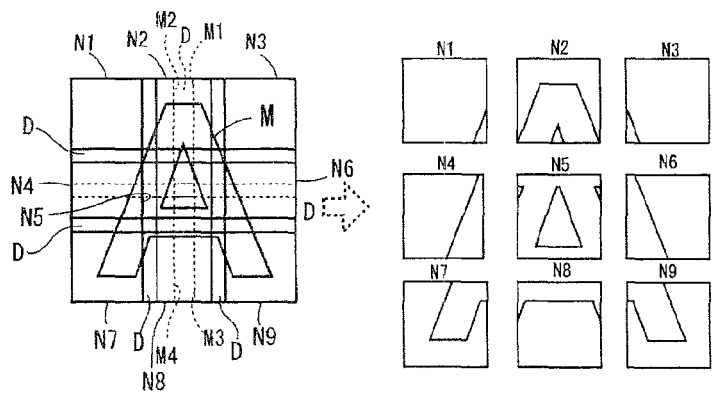
FIG. 4 is a diagram showing another mode of division of the model pattern.

The first embodiment has been so described that the model pattern M is divided into 2×2 elements by the model pattern dividing means 16 as shown in FIG. 2A. However, the arrangement may be such that pattern matching against the image pattern R is performed by dividing the model pattern M into 3×3 elements N1 to N9 as shown in FIG. 4, in addition to the above number of divisions, in such a manner that the division boundaries do not coincide with those of 2×2 divisions. In other words, the model pattern dividing means 16 in the second embodiment divides the model pattern M into the elements M1 to M4 and the elements N1 to N9, which are different in size from each other. And the shape corresponding to the model pattern M is recognized by the shape recognition means 17 whenever the model pattern M is divided in a different size. In this case, the arrangement may be such that the shape recognized in the 2×2 size is superposed on the shape recognized in the 3×3 size and the shape recognition means 17 recognizes the superposed portions as the shape corresponding to the model pattern M. In this manner, the elements in different sizes are combined for shape recognition, with the result that the model pattern M can be matched to the image pattern R with greater accuracy. Thus a mistaken judgment of the character string 4 correctly molded on the side 3 as nonconforming can be prevented when it is actually a conforming article.

That is, the model pattern dividing means 16 performs division of the model pattern M a plurality of times. And the model pattern dividing means 16 changes the number of divisions after each time of division such that the positions of the division boundaries of the elements M1 to M4 and the elements N1 to N9 divided at each time of division are dislocated from each other. In this way, the probability of matching some of the elements divided in different sizes with the image can be improved.

Thus, when the model pattern M is divided using the elements M1 to M4 and the elements N1 to N9, which are different in size from each other, it is of primary importance that the positions of the division boundaries of the elements divided at each time of division are dislocated from each other. Dislocation of the positions of the division boundaries ensures that the division boundaries of the model pattern M are supplemented by the elements divided in a different size. When the element positioning means 19 allocates the elements on the image pattern R, the whole of the image pattern R may be covered by the elements divided in different sizes. In other words, it is possible to better associate the model pattern M with the image pattern R. Therefore, a mistaken judgment of the character string 4 on the side 3 as nonconforming because of the occurrence of missing portions where the model pattern M cannot be allocated or the failure to match the model pattern M to the image pattern R can be prevented with better accuracy when the character string 4 is actually conforming.

In the second embodiment, the model pattern M divided in different sizes is matched against the image pattern R. Thus, by employing as the image pattern R only the portions where the elements in different sizes are superposed on each other, such as the portions where two pixels or more are superposed, the inspection can be performed with greater accuracy from this image pattern R by judging the character string 4 not correctly molded as nonconforming and the character string 4 correctly molded as conforming.

It is to be noted that the numbers of divisions of the model pattern M in the first embodiment and the second embodiment are only examples and may be altered as appropriate. The description thus far has dealt with the inspection of a character string 4 molded on the side 3 of a tire 2. However, the inspection object of this invention may be any pattern or the like formed on a product surface.

DESCRIPTION OF REFERENCE NUMERALS

1 inspection apparatus
5 inspection object imaging unit
6 pattern matching nit
11 image pattern generating means
12 model pattern storage
13 matching means
15 model pattern positioning means
16 model pattern dividing means
17 shape recognition means
18 element deforming means
19 element positioning means

The invention claimed is:

1. A tire appearance inspection apparatus for judging acceptability of an inspection tire by matching a model pattern representing conforming object data against an image captured of an appearance of the inspection tire, the apparatus comprising:
a model pattern positioning means for positioning the model pattern in a position with a highest degree of agreement by matching the model pattern against the image captured;
a model pattern dividing means for (i) dividing the model pattern into a plurality of elements in such a manner as to have mutually overlapping regions a plurality of times, and (ii) changing the number of divisions at each time of division so that positions of division boundaries of elements divided at each time of division are dislocated from the other; and
a shape recognition means for recognizing a shape corresponding to the model pattern by positioning each of the plurality of elements divided by the model pattern dividing means in a position with a highest degree of agreement by performing pattern matching within a predetermined range with reference to the position where the model pattern has been positioned on the image.

2. The tire appearance inspection apparatus according to claim 1, wherein the shape recognition means is provided with an element deforming means to carry out necessary deformation of the plurality of elements, including scaling deformation, rotational deformation, and shear deformation, and repeats the deformation of the plurality of elements by performing pattern matching against the image until the shape reaches a highest degree of agreement.

3. The tire appearance inspection apparatus according to claim 1,
wherein the model pattern dividing means divides the model pattern into 2×2 elements and divides the model pattern into 3×3 elements, and
wherein the shape recognition means recognizes a shape in a size of the 2×2 elements and a shape in a size of the 3×3 elements and superposes the shape recognized in the 2×2 size on the shape recognized in the 3×3 size.

* * * * *